United States Patent [19]

Prosl et al.

[11] Patent Number: 4,496,343
[45] Date of Patent: Jan. 29, 1985

[54] INFUSATE PUMP

[75] Inventors: Frank R. Prosl, Duxbury; Edward J. Sampson, Carlisle, both of Mass.

[73] Assignee: Infusaid Corporation, Norwood, Mass.

[21] Appl. No.: 577,301

[22] Filed: Feb. 6, 1984

Related U.S. Application Data

[63] Continuation of Ser. No. 388,483, Jun. 14, 1982, abandoned.

[51] Int. Cl.³ .................. A61M 5/00; A61M 31/00
[52] U.S. Cl. .................................. 604/86; 604/131; 604/141
[58] Field of Search ..................... 604/51–53, 604/83–86, 93, 131, 132, 139–141, 150–153, 890–892, 896

[56] References Cited

U.S. PATENT DOCUMENTS 3,613,663 10/1971 Johnson ........................ 604/86 X
3,951,147 4/1976 Tucker et al. .................... 604/891
4,000,740 1/1977 Mittleman ....................... 604/86
4,193,397 3/1980 Tucker et al. .................... 604/93 X
4,405,316 9/1983 Mittleman ....................... 604/86
4,416,661 11/1983 Norman et al. ................... 604/86

FOREIGN PATENT DOCUMENTS 2805354 9/1978 Fed. Rep. of Germany .
WO80/02377 11/1980 PCT Int'l Appl. ............... 604/891

Primary Examiner—John D. Yasko
Assistant Examiner—Michelle N. Lester
Attorney, Agent, or Firm—Cesari and McKenna

[57] ABSTRACT

Infusion apparatus includes a housing with an infusate chamber in the housing and means for conducting infusate from the chamber through a restrictive outlet passage to an additional small chamber having an entrance port closed by a self-sealing penetrable septum. An exit tube from the small chamber leads directly to a cannula at the infusion site so that liquid can be injected into the small chamber through its septum and delivered directly to the infusion site without backflowing into the infusate chamber.

7 Claims, 2 Drawing Figures

INFUSATE PUMP

This application is a continuation of application Ser. No. 388,483, filed June 14, 1982, now abandoned.

This invention relates to infusion apparatus. It relates especially to such apparatus which can be implanted and refilled and recharged periodically so that it can remain in the patient's body for a prolonged period.

BACKGROUND OF THE INVENTION

Relatively recently infusion apparatus has been developed which can be implanted in the body and remain there for a prolonged period. The apparatus can be refilled with infusate without having to remove the apparatus from the body. This refilling is accomplished by injecting additional infusate through a penetrable septum in the apparatus which septum is located directly under the patient's skin. In some cases, the act of refilling the apparatus with infusate also recharges the apparatus' power source so that the device can operate uninterruptedly to dispense infusate such as insulin, heparin or a chemotherapeutic agent at a very small rate over a long time. Examples of infusion apparatus of this general type are disclosed in U.S. Pat. Nos. 3,951,147 and 4,258,711, both owned by the assignee of the present application.

Some infusion apparatus of this type such as the one described in the latter patent have the capability of dispensing a continuous basal dose of infusate to the patient as well as larger bolus doses when the occasion demands it. For example, a patient may receive a continuous dose of insulin based on the average glucose level in his blood. Then, right after mealtimes, when the glucose level usually rises, the pump can be made to dispense a bolus dose of insulin to compensate for that increased glucose level due to the ingestion of food. In order to provide such dual dosage capability for any reasonable length of time, the pump must have a large infusate reservoir to provide both the basal and bolus requirements or two smaller reservoirs, one of which contains the infusate at the basal concentration and the other of which contains infusate at a higher bolus concentration. In either event, the inclusion of the bolus dispensing capability increases the overall size of the pump envelope.

In some instances, however, a supplement to the basal infusate flow is required relatively infrequently. For example, it may only be introduced to add an angiographic solution to the infusate so that the areal distribution in the body being infused can be monitored from time to time. It would be desirable in such cases to provide this capability in a pump having a minimum overall size or envelope. It is also essential that this added capability be provided without adversely affecting the basal infusate contained in the apparatus or its flow to the patient.

SUMMARY OF THE INVENTION

Accordingly, the present invention aims to provide improved infusion apparatus.

Another object of the invention is to provide infusion apparatus which can dispense infusate at a low basal rate to be supplemented by a dose of the same infusate or other liquid whenever that becomes desirable.

A further object of the invention is to provide implantable apparatus of this type which occupies a minimum amount of space in the patient's body.

Still another object of the invention is to provide an infusion pump whose infusate output to the patient can be supplemented when desired by a variety of other liquids without adversely affecting the dispensing of infusate.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

In general, the present pump can be situated outside or inside the body. Basically, it comprises an infusate reservoir, a pump for conducting infusate from that reservoir to a catheter positioned at an infusion site in the patient and a septum-sealed port in fluid communication with the flow path from the reservoir downstream from the pump which allows the fluid output from the pump to be supplemented by fluid injected into the port through its septum. The invention has particular application to implantable infusion apparatus. Accordingly, it will be described in that context. It should be understood, however, that it can also be applied to external infusion devices.

The pump includes a housing containing an infusate reservoir, preferably in the form of a metal bellows capsule. An entrance port into the interior of the bellows is closed by a penetrable septum mounted in the housing wall so that, when the apparatus is implanted, the septum is located directly under the patient's skin. An outlet port leading from the interior of the bellows capsule communicates with an outlet conduit which extends exteriorly of the housing. The bellows capsule is filled with infusate by percutaneous injection through the penetrable septum.

Means are provided inside the housing and outside the bellows for compressing the bellows, thereby to expel the infusate therein through the outlet conduit. One preferred means for exerting compressive force on the bellows capsule is a fluid pressure power cell such as disclosed in the aforesaid patents. Of course, various other battery-operated or mechanical devices may be employed to progressively compress the bellows. Flow of infusate from the capsule is maintained constant by a flow restriction in the outlet conduit.

Instead of leading directly to a catheter at the infusion site as described in those prior patents, the restricted outlet conduit from the bellows reservoir connects to the catheter by way of a small chamber located inside or outside the housing. The chamber is formed with an entry port containing a septum which is also located directly under the patient's skin when the apparatus is properly implanted. Various types of liquids can be introduced into this chamber by percutaneous injection through its septum. Those fluids will mix with the infusate being dispensed from the bellows reservoir and be conducted by the catheter to the same infusion site in the patient's body. These additive liquids may comprise radio-opaque material, higher concentrations of infusate or various other types of liquids depending upon the particular patient's medical problem. Since the chamber is located downstream from the flow restriction leading from the infusate reservoir, in practice almost all liquid injected into the chamber flows through the catheter to the infusion site.

Thus, the present pump has the capability of dispensing infusate for a prolonged period, with that infusate being supplemented when needed by slugs of other liquids which might be desirable for proper patient treatment. Yet this capability is achieved by a single device which is contained in a small envelope so that its implantation in the patient does not cause undue patient discomfort.

BRIEF DESCRIPTION OF THE DRAWING

For a fuller understanding of the nature and objects of the invention, reference should be had to the following detailed description, taken in connection with the accompanying drawing, in which.

DESCRIPTION OF THE PREFERRED EMBODIMENT

Figure 1:
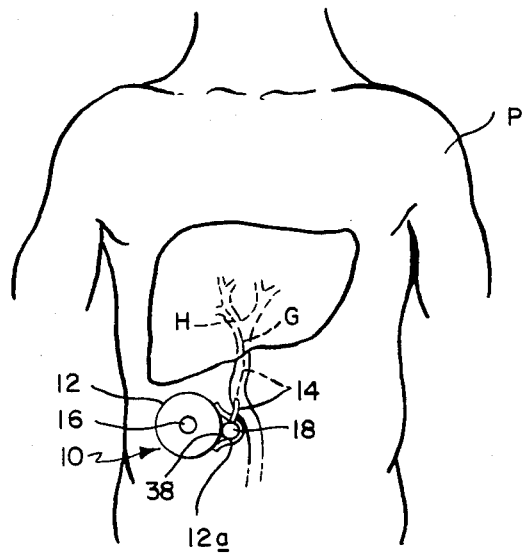
FIG. 1 is a diagrammatic view illustrating the infusion apparatus implanted in the body.

Referring to FIG. 1 of the drawing, the present apparatus indicated generally at 10 is shown implanted into a subcutaneous pocket in the abdominal wall of a patient P. The apparatus includes a generally cylindrical housing 12 which contains a supply of infusate. That infusate is dispensed from the apparatus through an unrestricted delivery cannula 14 leading from the housing 12 to an infusion site. In this case the cannula is shown implanted into the hepatic artery H via the gastroduodenal artery G.

When the supply of infusate in the housing 12 is exhausted, the apparatus can be refilled by subcutaneous injection through a self-sealing septum 16 in housing 12. When the apparatus is properly implanted, that septum is located directly under the patient's skin and is thus accessible to a syringe needle. In some pumps of this general type, that refilling operation also recharges the power source which expels the infusate from the housing 12 to the patient.

For some patients, the physician may wish to deliver a bolus dose of infusate to the patient or momentarily infuse another substance into the patient such as a radioopaque material for an angiogram, tracer dye microspheres which are opaque to X-rays or gamma rays. In the present apparatus, this is accomplished by subcutaneous injection through a second septum 18 located in an extension 12a of housing 12. Septum 18 is spaced from septum 16 on the same side of housing 12. Accordingly, it is also located directly under the skin and is equally accessible to penetration by a syringe needle.

The substance injected through septum 18 does not mix with the infusate in housing 12. Rather, it is delivered directly to cannula 14 so it flows immediately to the infusion site through the cannula. Accordingly, the patient receives the benefit of that substance immediately after its injection. The inclusion of the additional septum 18 gives the apparatus 10 the ability to deliver a slug of infusate or other liquid when needed without materially increasing the overall size of the apparatus. Accordingly, it makes the apparatus quite useful for those cases where it is desirable to deliver a second substance to a patient on an occasional basis.

Figure 2:
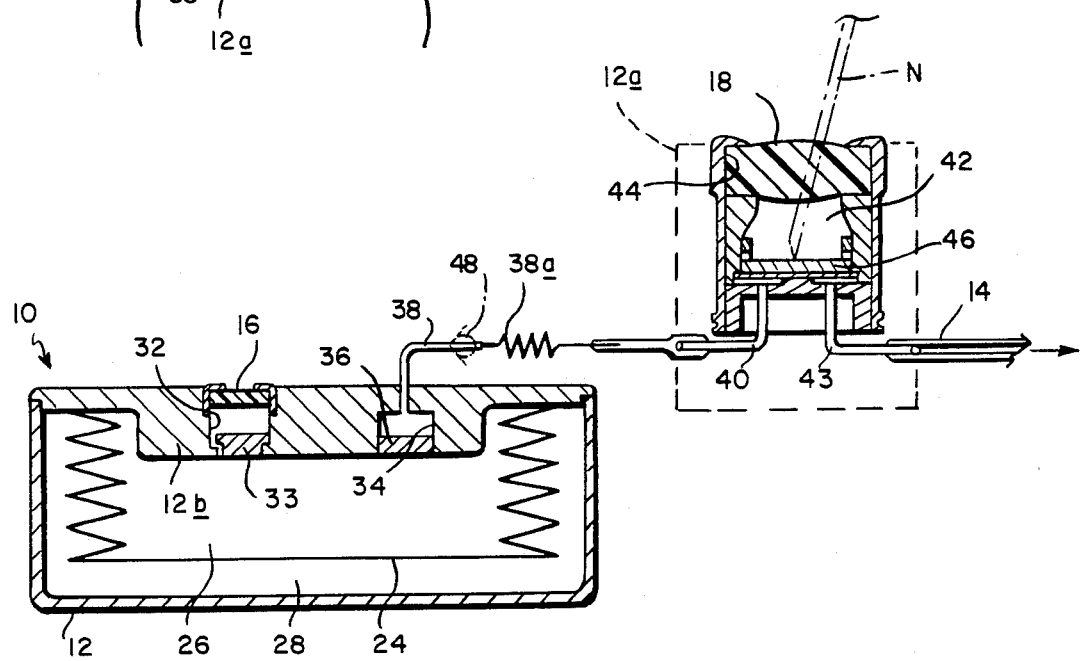
FIG. 2 is a sectional view on a much larger scale illustrating the elements of the FIG. 1 apparatus in greater detail.

Turning now to FIG. 2, the housing 12 is a generally cylindrical container which is about the size of a small hockey puck. The container is made of a suitable material such as titanium which is compatible with the human system. Positioned in the container is a bellows capsule 24 having an open end mounted to a header 12b at the top of the container 12, the opposite end of the bellows capsule being closed. Thus the bellows defines a first chamber 26 inside the bellows and a second chamber 28 outside the bellows, but inside the housing 12.

Formed in header 12b is an entry port 32 which extends from chamber 26 through header 12b. The outer end of port 32 is closed by the septum 16. A porous needle stop 33 is positioned at the inner end of port 32. Also formed in the header is an exit port 34 containing a filter 36. That port communicates with an outlet tube 38 containing a fluid restricter 38a and whose opposite end communicates with an inlet tube 40 leading to a small chamber 42 in the housing extension 12a. An exit tube 43 leads from the chamber 42 to cannula 14. Also, an entry port 44 is formed in the top of chamber 42 which port is closed by septum 18. Additionally, a needle stop 46 is positioned at the bottom of chamber 42.

Normally, chamber 26 is filled with infusate by injection of the infusate through septum 16. Chamber 28, on the other hand, is filled with two-phase fluid which vaporizes at physiological temperatures so that it exerts a pressure on the bellows capsule 24 tending to collapse it, thereby expelling the infusate through the exit port 34 and the restrictive outlet tube 38 to chamber 42. From that chamber the infusate flows through the cannula 14 to the infusion site, to wit, artery H (FIG. 1).

When the supply of infusate in chamber 26 is exhausted, it can be refilled by injecting additional infusate through septum 16 using a hypodermic syringe. The extension of the bellows capsule 24 during this refilling operation exerts a pressure on the two-phase fluid in chamber 28 which condenses that fluid thereby recharging the fluid power cell. The operation of such a fluid power cell is fully described in the aforesaid two patents, as well as in U.S. Pat. No. 3,731,681. Thus the infusate in chamber 26 can be dispensed to the patient at a very low flow rate to meet his long term requirements, the apparatus being refilled periodically, e.g. every thirty days, as needed.

In those situations where it would be desirable to infuse a larger concentration of the same infusate or a different liquid altogether into the patient's artery H, this is accomplished by injecting that additional liquid through septum 18 directly into chamber 42 using a standard hypodermic syringe shown in dotted lines at N in FIG. 2. That liquid then flows without restriction through outlet tube 43 and cannula 14 directly to the infusion site. Since chamber 42 is located downstream from restriction 38a, that additional substance is forced to flow directly through the cannula. Very little upstream flow through the restricted tube 38 into infusate chamber 26 will occur. Accordingly, substantially the entire volume (i.e. 99.99%) of the substance injected into chamber 42 flows immediately to the infusion site as a slug, rather than being dispensed to the patient over a longer term along with the infusate from chamber 26.

In those apparatus 10 having a very low restriction 38a in the outlet tube 38, such backflow from chamber 42 into chamber 26 may be prevented by a check valve in the outlet tube upstream from chamber 42. Such a valve is indicated in dotted lines at 48 in FIG. 2.

It can be seen therefore that the incorporation of chamber 42 with its septum 18 into the apparatus downstream from the restrictive outlet tube from the infusate reservoir 26 provides a convenient means for injecting additional liquids directly into the patient's arterial system whenever that is required. The incorporation of that additional chamber into the apparatus does not materially increase the volume of housing 12 or the overall cost or complexity of the apparatus. Yet it makes the apparatus much more versatile.

It will thus be seen that the objects set forth above, among those made apparent from the preceding description, are efficiently attained. Also, certain changes may be made in the above construction without departing from the scope of the invention. For example, a mechanical pump such as a peristaltic pump may be employed in lieu of the vapor pressure pump to conduct infusate from chamber 26 to catheter 16. Therefore, it is intended that all matter contained in the above description or shown in the accompanying drawing be interpreted as illustrative and not in a limiting sense.

It is also to be understood that the following claims are intended to cover all of the generic and specific features of the invention herein described.

What is claimed as new and desired to be secured by Letters Patent of the United States is:

1. Implantable infusion apparatus comprising:
   A. an infusate reservoir;
   B. an entry port into said infusate reservoir;
   C. a self-sealing penetrable septum closing said entry port;
   D. a small fixed-volume chamber;
   E. an entry port into said chamber;
   F. a second self-sealing penetrable septum closing the entry port into said chamber, the exposed surfaces of both said septa being located near one another in substantially the same plane or in parallel planes to that, when the apparatus is implanted in the body, both said septa are accessible extracorporeally by transcutaneous injection at nearby locations on the body surface;
   G. means defining a fluid inlet passage extending from said reservoir to said chamber;
   H. means for moving the contents of said reservoir to said chamber; and
   I. means defining a substantially unrestricted fluid outlet passage from said chamber for connection to a conduit leading to an infusion site so that an injection of infusate into said chamber flows substantially immediately to the infusion site.

2. Infusion apparatus comprising
   A. a housing;
   B. a container mounted inside the housing, said container defining along with the housing
      (1) a first chamber inside the container, and
      (2) a second chamber outside the container, but inside the housing;
   C. an entry port into one of said chambers;
   D. a self-sealing penetrable septum closing said entry port;
   E. a third small fixed-volume chamber;
   F. an entry port into the third chamber;
   G. a second self-sealing penetrable septum closing the entry port into the third chamber;
   H. means defining a fluid inlet passage extending from said one chamber to the third chamber;
   I. means in the other of said first and second chambers for moving the contents of said one chamber to said third chamber; and
   J. means defining a substantially unrestricted fluid outlet passage from the third chamber for connection to a cannula leading to an infusion site so that an injection of infusate into the third chamber flows substantially immediately to the infusion site.

3. The apparatus defined in claim 2 wherein said inlet passage defining means includes a fluid restriction.

4. The apparatus defined in claim 2 wherein the inlet passage defining means include check valve means for preventing fluid flow from said third chamber to said one chamber.

5. The apparatus defined in claim 2 wherein
   A. the container is collapsible; and
   B. the moving means comprise a fluid power cell contained in said other chamber for collapsing the container.

6. The apparatus defined in claim 2 wherein the first and second septa are spaced apart from one another on the same outside wall of said housing.

7. The infusion apparatus defined in claim 1 and further including means for inhibiting back-flow of fluid from said chamber to said reservoir.

* * * * *